United States Patent
Fack et al.

(10) Patent No.: US 8,802,066 B2
(45) Date of Patent: Aug. 12, 2014

(54) COSMETIC COMPOSITION COMPRISING A PARTICULAR ZINC SALT AND AN AMINO SILICONE

(75) Inventors: Géraldine Fack, Levallois (FR); Boris Lalleman, Paris (FR); Julie Brun, Asnieres sur Seine (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 13/995,980

(22) PCT Filed: Dec. 20, 2011

(86) PCT No.: PCT/EP2011/073344
§ 371 (c)(1),
(2), (4) Date: Sep. 10, 2013

(87) PCT Pub. No.: WO2012/084903
PCT Pub. Date: Jun. 28, 2012

(65) Prior Publication Data
US 2013/0340783 A1 Dec. 26, 2013

Related U.S. Application Data

(60) Provisional application No. 61/431,626, filed on Jan. 11, 2011.

(30) Foreign Application Priority Data

Dec. 21, 2010 (FR) .................................. 10 60902

(51) Int. Cl.
*A61K 8/00* (2006.01)
(52) U.S. Cl.
USPC ........................................ 424/70.1; 424/70.4
(58) Field of Classification Search
USPC .............................................. 424/70.1, 70.4
See application file for complete search history.

(56) References Cited

U.S. PATENT DOCUMENTS

| | | | |
|---|---|---|---|
| 2,261,002 A | 10/1941 | Ritter | |
| 2,271,378 A | 1/1942 | Searle | |
| 2,273,780 A | 2/1942 | Dittmar | |
| 2,375,853 A | 5/1945 | Kirby et al. | |
| 2,388,614 A | 11/1945 | Kirby et al. | |
| 2,454,547 A | 11/1948 | Bock et al. | |
| 2,961,347 A | 11/1960 | Floyd | |
| 3,206,462 A | 9/1965 | McCarty | |
| 3,227,615 A | 1/1966 | Korden | |
| 3,472,840 A | 10/1969 | Stone et al. | |
| 3,632,559 A | 1/1972 | Matter et al. | |
| 3,874,870 A | 4/1975 | Green et al. | |
| 3,910,862 A | 10/1975 | Barabas et al. | |
| 3,912,808 A | 10/1975 | Sokol | |
| 3,917,817 A | 11/1975 | Vanlerberghe et al. | |
| 3,929,990 A | 12/1975 | Green et al. | |
| 3,966,904 A | 6/1976 | Green et al. | |
| 3,986,825 A | 10/1976 | Sokol | |
| 4,001,432 A | 1/1977 | Green et al. | |
| 4,005,193 A | 1/1977 | Green et al. | |
| 4,013,787 A | 3/1977 | Varlerberghe et al. | |
| 4,025,617 A | 5/1977 | Green et al. | |
| 4,025,627 A | 5/1977 | Green et al. | |
| 4,025,653 A | 5/1977 | Green et al. | |
| 4,026,945 A | 5/1977 | Green et al. | |
| 4,027,008 A | 5/1977 | Sokol | |
| 4,027,020 A | 5/1977 | Green et al. | |
| 4,075,136 A | 2/1978 | Schaper | |
| 4,137,180 A | 1/1979 | Naik et al. | |
| 4,157,388 A | 6/1979 | Christiansen | |
| 4,165,367 A | 8/1979 | Chakrabarti | |
| 4,172,887 A | 10/1979 | Vanlerberghe et al. | |
| 4,185,087 A | 1/1980 | Morlino | |
| 4,189,468 A | 2/1980 | Vanlerberghe et al. | |
| 4,197,865 A | 4/1980 | Jacquet et al. | |
| 4,217,914 A | 8/1980 | Jacquet et al. | |
| 4,223,009 A | 9/1980 | Chakrabarti | |
| 4,240,450 A | 12/1980 | Grollier et al. | |
| 4,277,581 A | 7/1981 | Vanlerberghe et al. | |
| 4,348,202 A | 9/1982 | Grollier et al. | |
| 4,349,532 A | 9/1982 | Vanlerberghe et al. | |
| 4,381,919 A | 5/1983 | Jacquet et al. | |

(Continued)

FOREIGN PATENT DOCUMENTS

EP    0 080 976 A1    6/1983
EP    0 095 238 A2    11/1983

(Continued)

OTHER PUBLICATIONS

STIC Search Report dated Oct. 23, 2013.*
International Search Report for PCT/EP2011/073344.
Herrwert, S. et al., "Silicone Quaternium-22: New Silicone Technology for Premium Hair Conditioning with Additional Benefits," SOFW-Journal Seifen, Oele, Fette, Wachse, Verlag Fur Chemische Industrie, Augsburg, DE, vol. 135, No. 6, Jun. 1, 2009, XP002584466, pp. 11-12, 14.
Croda Inc.: "The Use of Monasil PCA, Arlasilk Phospholipid PLN and/or MONASIL PDM as a Hair Colour Protectant," Research Disclosure, Mason Publications, Hampshire, GB, vol. 523, No. 3, Nov. 1, 2007, XP007137712, p. 1083.
Croda Inc.: "The Use of MONASIL PCA, Arlasilk Phospholipid PLN and/or MONASIL PDM as a Hair Colour Protectant," Research Disclosure, Mason Publications, Hampshire, GB, vol. 523, No. 3, XP007137712, ISSN: 0374-4353, Nov. 1, 2007, p. 1083, the whole document.

(Continued)

*Primary Examiner* — Eisa Elhilo
(74) *Attorney, Agent, or Firm* — The Marbury Law Group, PLLC

(57) ABSTRACT

The present invention relates to a cosmetic composition comprising, in a cosmetically acceptable medium, at least one non-nitrogenous zinc salt and at least one amino silicone, in a weight ratio of the amount of amino silicone(s) to the amount of zinc element ranging from 0.01 to 5, preferably from 0.2 to 3. Another subject of the invention relates to a treatment process for keratin fibers, using such a composition, and the use of such a composition, preferably in the form of a leave-in care product, for conditioning keratin fibers and protecting the artificial color thereof against fading.

17 Claims, No Drawings

(56) References Cited

U.S. PATENT DOCUMENTS

| | | | |
|---|---|---|---|
| 4,390,689 A | 6/1983 | Jacquet et al. |
| 4,422,853 A | 12/1983 | Jacquet et al. |
| 4,445,521 A | 5/1984 | Grollier et al. |
| 4,579,732 A | 4/1986 | Grollier et al. |
| 4,608,250 A | 8/1986 | Jacquet et al. |
| 4,702,906 A | 10/1987 | Jacquet et al. |
| 4,719,099 A | 1/1988 | Grollier et al. |
| 4,719,282 A | 1/1988 | Nadolsky et al. |
| 4,777,040 A | 10/1988 | Grollier et al. |
| 4,839,166 A | 6/1989 | Grollier et al. |
| 4,874,554 A | 10/1989 | Lange et al. |
| 4,948,579 A | 8/1990 | Jacquet et al. |
| 4,970,066 A | 11/1990 | Grollier et al. |
| 4,996,059 A | 2/1991 | Grollier et al. |
| 5,009,880 A | 4/1991 | Grollier et al. |
| 5,089,252 A | 2/1992 | Grollier et al. |
| 5,196,189 A | 3/1993 | Jacquet et al. |
| 5,374,334 A | 12/1994 | Sommese et al. |
| 5,958,392 A | 9/1999 | Grollier et al. |
| 6,426,383 B1 | 7/2002 | Fong et al. |
| 6,824,765 B2 | 11/2004 | Gawtrey et al. |
| 6,894,110 B2 | 5/2005 | Fong et al. |
| 7,220,408 B2 | 5/2007 | Decoster et al. |
| 7,504,094 B2 | 3/2009 | Decoster et al. |
| 7,713,310 B2 | 5/2010 | Lalleman |
| 2003/0147827 A1 | 8/2003 | Decoster et al. |
| 2004/0010863 A1 | 1/2004 | Gawtrey et al. |
| 2006/0067907 A1 | 3/2006 | Mougin et al. |
| 2007/0009472 A1* | 1/2007 | Niebauer et al. .......... 424/70.28 |
| 2007/0154434 A1 | 7/2007 | Decoster et al. |
| 2008/0134449 A1 | 6/2008 | Lalleman |
| 2008/0229521 A1 | 9/2008 | Lalleman |
| 2009/0074695 A1* | 3/2009 | Mahe et al. .............. 424/70.11 |
| 2009/0176674 A1 | 7/2009 | Peffly et al. |
| 2009/0176675 A1* | 7/2009 | Peffly et al. ................. 510/121 |
| 2010/0035782 A1 | 2/2010 | Decoster et al. |
| 2010/0147319 A1 | 6/2010 | Lalleman |
| 2010/0147320 A1 | 6/2010 | Lalleman |

FOREIGN PATENT DOCUMENTS

| | | |
|---|---|---|
| EP | 0 122 324 A1 | 10/1984 |
| EP | 0 337 354 A1 | 10/1989 |
| EP | 0 530 974 A1 | 3/1993 |
| EP | 1 312 334 A2 | 5/2003 |
| EP | 1 312 346 A2 | 5/2003 |
| EP | 1 923 042 A1 | 5/2008 |
| EP | 2 143 417 A1 | 1/2010 |
| FR | 1 492 597 | 8/1967 |
| FR | 1 583 363 | 10/1969 |
| FR | 2 077 143 | 10/1971 |
| FR | 2 080 759 | 11/1971 |
| FR | 2 162 025 | 7/1973 |
| FR | 2 190 406 | 2/1974 |
| FR | 2 280 361 | 2/1975 |
| FR | 2 252 840 | 6/1975 |
| FR | 2 270 846 | 12/1975 |
| FR | 2 316 271 | 1/1977 |
| FR | 2 320 330 | 3/1977 |
| FR | 2 336 434 | 7/1977 |
| FR | 2 368 508 | 5/1978 |
| FR | 2 383 660 | 10/1978 |
| FR | 2 393 573 | 1/1979 |
| FR | 2 413 907 | 8/1979 |
| FR | 2 470 596 | 5/1981 |
| FR | 2 519 863 | 7/1983 |
| FR | 2 598 611 A1 | 11/1987 |
| FR | 2 875 503 A1 | 3/2006 |
| GB | 1 546 809 | 5/1979 |
| WO | 2007/005577 A2 | 1/2007 |
| WO | 2007/021604 A2 | 2/2007 |

OTHER PUBLICATIONS

Herrwert S., et al., "Silicone Quaternium-22: New Silicone Technology for Premium Hair Conditioning with Additional Benefits," Sofw—Journal Seifen, Oele, Fette, Wachse, Verlag Fur Chemische Industrie,Augsburg, De, vol. 135, No. 6, XP002584466, ISN: 0942-7694, Jun. 1, 2009, pp. 11-17.

* cited by examiner

COSMETIC COMPOSITION COMPRISING A PARTICULAR ZINC SALT AND AN AMINO SILICONE

This is a national stage application of PCT/EP2011/073344, filed internationally on Dec. 20, 2011, which claims priority to U.S. Provisional Application No. 61/431,626, filed on Jan. 11, 2011; as well as French Application FR 1060902, filed on Dec. 21, 2010.

The present invention relates to a cosmetic composition comprising at least one particular zinc salt and at least one amino silicone in a particular weight ratio, and also to the use of such a composition, preferably in the form of a rinse-out or leave-in care product, for conditioning keratin fibres and protecting the artificial colour thereof against fading.

It is known practice to dye the hair with dyeing compositions containing oxidation dye precursors, which are generally called oxidation bases. These oxidation bases are colourless or weakly coloured compounds, which, when combined with oxidizing products, give rise to coloured compounds via a process of oxidative condensation. It is also known that the shades obtained with these oxidation bases can be varied by combining them with couplers or coloration modifiers. The variety of molecules used as oxidation bases and as couplers allows a wide range of colours to be obtained.

It is also known practice to dye the hair by direct dyeing. The process conventionally used in direct dyeing consists in applying to the hair direct dyes, which are coloured or colouring molecules that have affinity for the hair, in leaving them to act, and then in rinsing the fibres.

The colourations which result therefrom are particularly chromatic colourations which are, however, temporary or semi-permanent since the nature of the interactions that bind the direct dyes to the keratin fibre and their desorption from the surface and/or from the core of the fibre are responsible for their weak dyeing power and for their poor wash-fastness.

The artificial colour of hair, provided by a direct or oxidation dyeing treatment gradually attenuates as a result of repeated washing and of exposure to light, leading, over time, to fading of the colouration of the hair.

Apart from the detrimental change in the artificial colours, the hair is also damaged as a result of repeated washing, of various dyeing-bleaching treatments and also of mechanical treatments such as passing through a comb or a brush. Generally, care products such as conditioners, masks or leave-in care products which make it possible to give the hair great beauty by providing a good level of treatment are used. The use of silicones in such care products is known.

However, the formulation of zinc salts in such care products poses many difficulties; inter alia, the formulation of zinc salts, in particular in the presence of cationic silicone agents, results in compositions which most commonly are not stable over time and are not therefore marketable.

Thus, there is a need to find cosmetic compositions, in particular in the form of a leave-in care product, which make it possible both to protect the artificial colour of the hair against the various attacks responsible for fading of the colours (repeated washing, sunlight) and to provide the hair with a good level of care, and which are stable over time.

The applicant has discovered, surprisingly, that by formulating cosmetic compositions comprising at least one particular zinc salt and at least one amino silicone in a particular ratio, it is possible to remedy the drawbacks mentioned above, while obtaining compositions which are stable over time, which provide satisfactory protection of the artificial colour of the hair against fading of the colouration of the hair, and which give the hair good cosmetic properties.

In particular, the composition according to the invention is stable over time. In particular, it has a satisfactory storage stability both at ambient temperature (25° C.) and at higher temperature (37 or 45° C., for example). This means that the composition of the invention has a texture which changes little or not at all over time and in particular which does not exhibit a syneresis effect over time.

In addition, the composition according to the invention makes it possible to obtain hair which is more supple, smoother to the touch and better coated.

Thus, a subject of the invention is a cosmetic composition comprising:
  one or more non-nitrogenous zinc salts, and
  one or more amino silicones,
in a ratio by weight of the amount of amino silicone(s) to the amount of zinc element ranging from 0.01 to 5.

Another subject of the present invention consists of a cosmetic treatment process for keratin fibres, preferably human keratin fibres such as the hair, in which a composition according to the invention is applied to the keratin fibres and the scalp.

Another subject of the present invention relates to the use of a composition according to the invention, preferably in the form of a leave-in care product such as a conditioner, for conditioning keratin fibres, preferably human keratin fibres such as the hair, and protecting the artificial colour thereof against fading of the colours.

Other subjects, characteristics, aspects and advantages of the invention will become more clearly apparent on reading the description and the examples which follow.

The composition according to the invention is preferably a leave-in composition, and in particular a composition comprising preferably less than 3% by weight, more preferentially less than 1% by weight, relative to the total weight of the composition, and even better still not comprising anionic, nonionic, amphoteric or zwitterionic surfactants.

The term "non-nitrogenous zinc salt" is intended to mean any inorganic or organic compound comprising in its structure at least one zinc-based cation and an anion derived from an inorganic or organic acid, said salt not comprising a nitrogen atom in its structure.

The zinc salt(s) is (are) chosen from water-soluble zinc salts, which are in particular inorganic or organic, and mixtures thereof.

The term "water-soluble zinc salt" is intended to mean any salt which has a solubility in water greater than or equal to 0.5% by weight, at a temperature of 25° C.

Among the water-soluble zinc salts that can be used according to the present invention, mention may be made of zinc sulphate, zinc chloride, zinc lactate, zinc gluconate, zinc phenolsulphonate, zinc citrate, zinc salicylate and its derivatives, and mixtures thereof.

Zinc salicylate and its derivatives according to the invention correspond to the following formula:

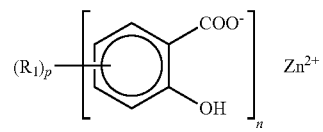

in which:
  n=2, p=0, 1, 2 or 3; and
  $R_1$ denotes a linear or branched $C_1$-$C_{18}$ alkyl group (for example methyl, ethyl, n-propyl, isopropyl, n-butyl); a linear or branched $C_1$-$C_{18}$ hydroxyalkyl group; a halogen atom (for example iodine, bromine or chlorine), a $C_2$-$C_{18}$ acyl group (for example acetyl); or a $COR_2$ or $OCOR_2$ or $CONHR_2$ group where $R_2$ denotes a hydrogen atom or a linear or branched $C_1$-$C_{18}$ alkyl group.

Preferentially, the zinc salt(s) is (are) chosen from zinc sulphate, zinc chloride, zinc lactate, zinc gluconate, zinc salicylate and zinc citrate, and mixtures thereof.

Even better still, the zinc salt(s) is (are) chosen from zinc sulphate, zinc chloride, zinc lactate and zinc gluconate, alone or as a mixture.

Even more preferentially, the zinc salt is an inorganic zinc salt. Even more preferentially, the zinc salt is zinc lactate or zinc gluconate; even better still the zinc salt is zinc gluconate.

In the composition according to the invention, the zinc gluconate is sold, for example, under the name Givobio G Zn by the company SEPPIC.

The composition according to the invention preferably comprises from 0.1 to 10% by weight of zinc salt(s), in particular from 0.3 to 8%, better still from 0.4 to 7% by weight, or even from 0.5 to 6.5% by weight, relative to the total weight of the composition.

The concentration of zinc element is preferably less than 2% by weight, in particular ranging from 0.005% to 1.5% by weight, and even better still from 0.1% to 1% by weight, relative to the total weight of the composition.

The composition according to the invention comprises one or more amino silicone(s).

The term "amino silicone" means any silicone comprising at least one primary, secondary or tertiary amine function or a quaternary ammonium group.

The amino silicones used in the cosmetic composition according to the present invention are chosen from:
(a) the compounds corresponding to formula (I) below:

$$(R^1)_a(T)_{3-a}\text{-Si}[OSi(T)_2]_n\text{-}[OSi(T)_b(R^1)_{2-b}]_m\text{-}OSi(T)_{3-a}\text{-}(R^1)_a$$

in which,

T is a hydrogen atom or a phenyl, hydroxyl (—OH) or $C_1$-$C_8$ alkyl radical, and preferably methyl, or a $C_1$-$C_8$ alkoxy radical, preferably methoxy, a denotes the number 0 or an integer from 1 to 3, and preferably 0, b denotes 0 or 1, and in particular 1, m and n are numbers such that the sum (n+m) can range especially from 1 to 2000 and in particular from 50 to 150, it being possible for n to denote a number from 0 to 1999 and in particular from 49 to 149, and for m to denote a number from 1 to 2000 and in particular from 1 to 10;

$R_1$ is a monovalent radical of formula —$C_qH_{2q}L$ in which q is a number from 2 to 8 and L is an optionally quaternized amino group chosen from the groups:

—N($R^2$)—$CH_2$—$CH_2$—N($R^2$)$_2$;
—N($R^2$)$_2$; —N$^+$($R^2$)$_3$Q$^-$;
—N$^+$($R^2$)(H)$_2$Q$^-$;
—N$^+$($R^2$)$_2$HQ$^-$;
—N($R^2$)—$CH_2$—$CH_2$—N$^+$($R^2$)(H)$_2$Q$^-$, in which $R^2$ can denote a hydrogen atom, a phenyl, a benzyl or a saturated monovalent hydrocarbon-based radical, for example a $C_1$-$C_{20}$ alkyl radical, and Q$^-$ represents a halide ion such as, for example, fluoride, chloride, bromide or iodide. In particular, the amino silicones corresponding to the definition of formula (I) are chosen from the compounds corresponding to the following formula:

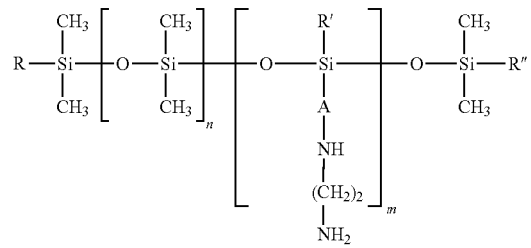

(II)

in which R, R' and R", which may be identical or different, denote a $C_1$-$C_4$ alkyl radical, preferably $CH_3$; a $C_1$-$C_4$ alkoxy radical, preferably methoxy; or OH; A represents a linear or branched, $C_3$-$C_8$ and preferably $C_3$-$C_6$ alkylene radical; m and n are integers dependent on the molecular weight and the sum of which is between 1 and 2000.

According to a first possibility, R, R' and R", which may be identical or different, represent a $C_1$-$C_4$ alkyl or hydroxyl radical, A represents a $C_3$ alkylene radical and m and n are such that the weight-average molecular weight of the compound is between 5000 and 500 000 approximately. The compounds of this type are called "amodimethicone" in the CTFA dictionary.

According to a second possibility, R, R' and R", which may be identical or different, represent a $C_1$-$C_4$ alkoxy or hydroxyl radical, at least one of the radicals R or R" is an alkoxy radical and A represents a $C_3$ alkylene radical. The hydroxy/alkoxy molar ratio is preferably between 0.2/1 and 0.4/1 and advantageously equal to 0.3/1. Moreover, m and n are such that the weight-average molecular weight of the compound is between 2000 and $10^6$. More particularly, n is between 0 and 999 and m is between 1 and 1000, the sum of n and m being between 1 and 1000.

In this category of compounds, mention may be made, inter alia, of the product Belsil® ADM 652 sold by Wacker.

According to a third possibility, R and R", which are different, represent a $C_1$-$C_4$ alkoxy or hydroxyl radical, at least one of the radicals R or R" is an alkoxy radical, R' represents a methyl radical and A represents a $C_3$ alkylene radical. The hydroxy/alkoxy molar ratio is preferably between 1/0.8 and 1/1.1, and advantageously is equal to 1/0.95. Moreover, m and n are such that the weight-average molecular weight of the compound is between 2000 and 200 000. More particularly, n is between 0 and 999 and m is between 1 and 1000, the sum of n and m being between 1 and 1000.

More particularly, mention may be made of the product Fluid WR® 1300 sold by Wacker.

According to a fourth possibility, R and R" represent a hydroxyl radical, R' represents a methyl radical and A is a $C_4$-$C_8$ and preferably $C_4$ alkylene radical. Moreover, m and n are such that the weight-average molecular weight of the compound is between 2000 and $10^6$. More particularly, n is between 0 and 1999 and m is between 1 and 2000, the sum of n and m being between 1 and 2000.

A product of this type is especially sold under the name DC 28299 by Dow Corning.

It should be noted that the molecular weight of these silicones is determined by gel permeation chromatography (ambient temperature, polystyrene standard; μ styragel columns; eluent THF; flow rate of 1 mm/min; 200 μl of a solution containing 0.5% by weight of silicone in THF are injected and the detection is carried out by refractometry and UV-metry).

A product corresponding to the definition of formula (II) is in particular the polymer called "trimethylsilylamodimethicone" in the CTFA dictionary, corresponding to formula (III) below:

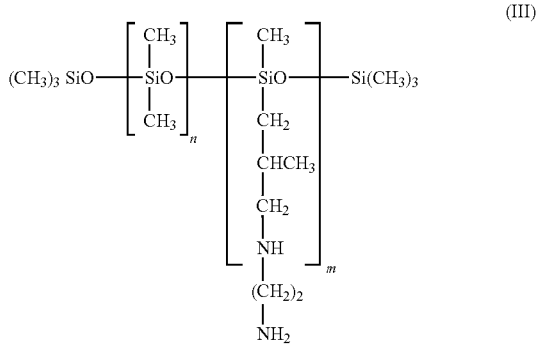

(III)

in which n and m have the meanings given above in accordance with formula (I). Such compounds are described, for example, in EP 95238; a compound of formula (III) is, for example, sold under the name Q2-8220 by the company OSI;

(b) the compounds corresponding to formula (IV) below:

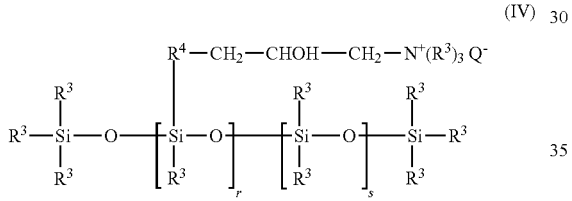

(IV)

in which, $R^3$ represents a $C_1$-$C_{18}$ monovalent hydrocarbon-based radical, and in particular a $C_1$-$C_{18}$ alkyl or $C_2$-$C_{18}$ alkenyl radical, for example methyl;

$R^4$ represents a divalent hydrocarbon-based radical, in particular a $C_1$-$C_{18}$ alkylene radical or a $C_1$-$C_{18}$ divalent alkyleneoxy radical, for example comprising from 1 to 8 carbons atoms;

$Q^-$ is a halide ion, in particular chloride;

r represents a mean statistical value from 2 to 20 and in particular from 2 to 8;

s represents a mean statistical value from 20 to 200 and in particular from 20 to 50.

Such compounds are described more particularly in patent U.S. Pat. No. 4,185,087.

A compound falling within this class is the product sold by the company Union Carbide under the name Ucar Silicone ALE 56;

(c) the quaternary ammonium silicones of formula (V):

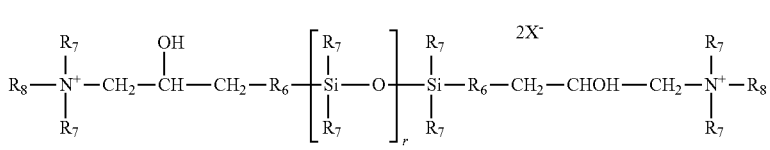

(V)

in which:

$R_7$, which may be identical or different, represent a monovalent hydrocarbon-based radical containing from 1 to 18 carbon atoms, and in particular a $C_1$-$C_{18}$ alkyl radical, a $C_2$-$C_{18}$ alkenyl radical or a ring comprising 5 or 6 carbon atoms, for example methyl;

$R_6$ represents a divalent hydrocarbon-based radical, especially a $C_1$-$C_{18}$ alkylene radical or a divalent $C_1$-$C_{18}$, and for example $C_1$-$C_8$, alkyleneoxy radical linked to the Si via an SiC bond;

$R_8$, which may be identical or different, represent a hydrogen atom, a monovalent hydrocarbon-based radical containing from 1 to 18 carbon atoms, and in particular a $C_1$-$C_{18}$ alkyl radical, a $C_2$-$C_{18}$ alkenyl radical or a radical —$R_6$—NH-COR$_7$;

$X^-$ is an anion such as a halide ion, especially chloride, or an organic acid salt (acetate, etc.);

r represents a mean statistical value from 2 to 200 and in particular from 5 to 100.

These silicones are, for example, described in application EP-A-0530974;

(d) the amino silicones of the formula (VI):

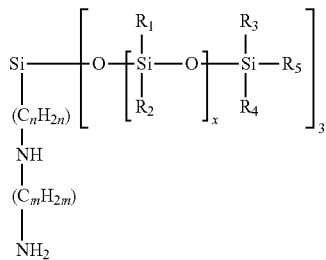

in which:

$R_1$, $R_2$, $R_3$ and $R_4$, which may be identical or different, denote a $C_1$-$C_4$ alkyl radical or a phenyl group, $R_5$ denotes a $C_1$-$C_4$ alkyl radical or a hydroxyl group, n is an integer ranging from 1 to 5, m is an integer ranging from 1 to 5, and in which x is selected such that the amine number is between 0.01 and 1 meq/g.

The silicone which is particularly preferred is an amodimethicone.

The composition according to the invention can comprise 0.01 to 10% by weight of amino silicone(s), preferably 0.05 to 5% by weight, and even better still 0.1 to 3%, relative to the total weight of the composition.

The weight ratio of the amount of amino silicones to the amount of zinc element ranges from 0.01 to 5, better still from 0.1 to 3, even better still from 0.2 to 2.

The weight ratio of the amount of amino silicone to the amount of zinc salt(s) ranges preferably from 0.005 to 10, better still from 0.01 to 1.

The composition according to the invention can comprise one or more esters of a fatty alcohol and/or of a fatty acid, and preferably of a saturated fatty acid and of a saturated fatty monoalcohol.

The fatty esters used in the composition of the invention are preferably saturated fatty acid esters, i.e. esters of saturated carboxylic acids containing at least 10 carbon atoms, and of saturated fatty monoalcohols containing at least 10 carbon atoms. The saturated acids or monoalcohols may be linear or branched. The saturated carboxylic acids preferably contain from 10 to 30 carbon atoms and more particularly from 12 to 24 carbon atoms. They may be optionally hydroxylated. The saturated fatty monoalcohols preferably comprise from 10 to 30 carbon atoms and more particularly from 12 to 24 carbon atoms. Preferably, the fatty esters of the invention are solid at 25° C. and at atmospheric pressure.

Preferably, the fatty esters are chosen from myristyl myristate, cetyl myristate, stearyl myristate, myristyl palmitate, cetyl palmitate, stearyl palmitate, myristyl stearate, cetyl stearate, stearyl stearate and behenyl behenate, and mixtures thereof.

The composition according to the invention preferably comprises from 0.01 to 10%, and better still from 0.1 to 5% by weight of fatty alcohol and/or acid ester(s), relative to the total weight of the composition.

The composition according to the invention may also comprise one or more fatty alcohols.

For the purpose of the present invention, the term "fatty alcohol" is intended to mean any saturated or unsaturated, linear or branched, pure fatty alcohol containing at least 8 carbon atoms and not any comprising oxyalkylenated or glycerolated groups.

The fatty alcohol may have the structure R—OH, in which R denotes a saturated or unsaturated, linear or branched radical containing from 8 to 40 carbon atoms and preferably from 8 to 30; R preferably denotes a $C_{12}$-$C_{24}$ alkyl or $C_{12}$-$C_{24}$ alkenyl group. R may be substituted with one or more hydroxyl groups.

By way of example of fatty alcohols, mention may be made of lauryl alcohol, myristyl alcohol, cetyl alcohol, dodecyl alcohol, decyl alcohol, stearyl alcohol, oleyl alcohol, behenyl alcohol, linoleyl alcohol, undecylenyl alcohol, palmitoleyl alcohol, arachidonyl alcohol and erucyl alcohol, and mixtures thereof.

The fatty alcohol may represent a mixture of fatty alcohols, which means that several species of fatty alcohol may coexist, in the form of a mixture, in a commercial product.

By way of a mixture of fatty alcohols, mention may be made of cetylstearyl alcohol or cetearyl alcohol.

Among all the fatty alcohols that can be used according to the invention, one or more fatty alcohols chosen from cetyl alcohol, stearyl alcohol and myristyl alcohol is (are) preferably used.

In the event of said fatty alcohols being present, the composition according to the invention may comprise preferably from 0.1 to 10%, and even better still from 1 to 5% by weight of fatty alcohol(s), relative to the total weight of the composition.

The composition according to the invention may also comprise one or more cationic surfactants chosen from the following quaternary ammonium salts:

quaternary ammonium salts of formula (VII) below:

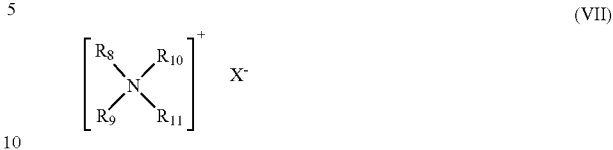

(VII)

in which the radicals $R_8$ to $R_{11}$, which may be identical or different, represent an aromatic radical such as aryl or alkylaryl or a linear or branched aliphatic radical containing from 1 to 30 carbon atoms, at least one of the radicals $R_8$ to $R_{10}$ comprising an alkyl or alkenyl radical containing from 8 to 30 carbon atoms, preferably from 14 to 30 carbon atoms, and even better still from 16 to 25 carbon atoms, it being possible for the aliphatic radicals to comprise heteroatoms such as, in particular, oxygen, nitrogen, sulphur and halogens.

The aliphatic radicals are, for example, chosen from the following radicals: alkyl, alkoxy, polyoxy($C_2$-$C_6$)alkylene, alkylamide, ($C_{12}$-$C_{22}$)alkylamido($C_2$-$C_6$)alkyl, ($C_{12}$-$C_{22}$) alkyl acetate, hydroxyalkyl, containing approximately from 1 to 30 carbon atoms, preferably from 14 to 30 and even better still from 16 to 25 carbon atoms; $X^-$ is an anion chosen from the group of halides, such as chloride, phosphates, acetates, lactates, ($C_2$-$C_6$)alkyl sulphates, and alkyl- or alkylarylsulphonates, such as methosulphate.

Among the quaternary ammonium salts of formula (I), use is preferably made of the alkyltrimethylammonium chlorides in which the alkyl radical contains approximately from 12 to 22 carbon atoms, in particular the behenyltrimethylammonium or cetyltrimethylammonium salts, or else the oleocetyldimethylhydroxyethylammonium salts;

quaternary ammonium salts of imidazoline, for instance those of formula (VIII) below:

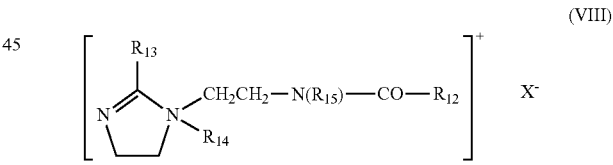

(VIII)

in which, $R_{12}$ represents an alkenyl or alkyl group containing from 8 to 30 carbon atoms, for example tallow fatty acid derivatives, $R_{13}$ represents a hydrogen atom, a $C_1$-$C_4$ alkyl group, or an alkenyl or alkyl group containing from 8 to 30 carbon atoms, $R_{14}$ represents a $C_1$-$C_4$ alkyl group, $R_{15}$ represents a hydrogen atom or a $C_1$-$C_4$ alkyl group, and $X^-$ is an anion chosen from the group of halides, phosphates, acetates, lactates, ($C_1$-$C_4$)alkyl sulphates, and ($C_1$-$C_4$)alkyl- or ($C_1$-$C_4$)alkylarylsulphonates. $R_{12}$ and $R_{13}$ preferably denote a mixture of alkyl or alkenyl groups containing from 12 to 21 carbon atoms, for example tallow fatty acid derivatives, $R_{14}$ denotes a methyl group, and $R_{15}$ denotes a hydrogen atom. Such a product is, for example, sold under the name Rewoquat® W 75 by the company Rewo;

di- or triquaternary ammonium salts, in particular of formula (IX) below:

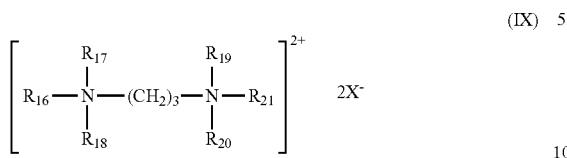

in which $R_{16}$ denotes an alkyl group containing approximately from 16 to 30 carbon atoms, which is optionally hydroxylated and/or interrupted with one or more oxygen atoms; $R_{17}$ is chosen from hydrogen, an alkyl group containing from 1 to 4 carbon atoms or a group $-(CH_2)_3-N^+(R_{16a})(R_{17a})(R_{18a})$; $R_{16a}$, $R_{17a}$, $R_{18a}$, $R_{18}$, $R_{19}$, $R_{20}$ and $R_{21}$, which may be identical or different, are chosen from hydrogen and an alkyl group containing from 1 to 4 carbon atoms, and $X^-$ is an anion chosen from the group of halides, acetates, phosphates, nitrates, $(C_1$-$C_4)$alkyl sulphates, and $(C_1$-$C_4)$alkyl- or $(C_1$-$C_4)$alkylarylsulphonates, in particular methyl sulphate and ethyl sulphate. Such compounds are, for example, Finquat CT-P, sold by the company Finetex (Quaternium 89), and Finquat CT, sold by the company Finetex (Quaternium 75);

quaternary ammonium salts containing one or more ester functions, such as, for example, those of formula (X) below:

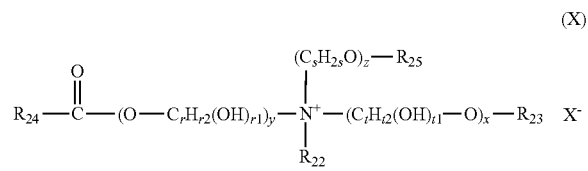

in which:
$R_{22}$ is chosen from $C_1$-$C_6$ alkyl groups and $C_1$-$C_6$ hydroxyalkyl or dihydroxyalkyl groups,
$R_{23}$ is chosen from:
  the group $R_{26}$—C(O)—,
  linear or branched, saturated or unsaturated, $C_1$-$C_{22}$ hydrocarbon-based groups $R_{27}$,
  a hydrogen atom,
$R_{25}$ is chosen from:
  the group $R_{28}$—C(O)—,
  linear or branched, saturated or unsaturated, $C_1$-$C_6$ hydrocarbon-based groups $R_{29}$,
  a hydrogen atom,
$R_{24}$, $R_{26}$ and $R_{28}$, which may be identical or different, are chosen from linear or branched, saturated or unsaturated, $C_7$-$C_{21}$ hydrocarbon-based groups,
r, s and t, which may be identical or different, are integers ranging from 2 to 6,
r1 and t1, which may be identical or different, are 0 or 1,
r2+r1=2r et t1+t2=2t,
y is an integer ranging from 1 to 10,
x and z, which may be identical or different, are integers ranging from 0 to 10,
$X^-$ is a simple or complex, organic or inorganic anion,
with the proviso that the sum x+y+z is from 1 to 15, that when x is 0, then $R_{23}$ denotes $R_{27}$, and that when z is 0, then $R_{25}$ denotes $R_{29}$.

The alkyl groups $R_{22}$ may be linear or branched, and more particularly linear.

Preferably, $R_{22}$ denotes a methyl, ethyl, hydroxyethyl or a dihydroxypropyl group, and more particularly a methyl or ethyl group.

Advantageously, the sum x+y+z is from 1 to 10.

When $R_{23}$ is a hydrocarbon-based group $R_{27}$, it may be long and contain from 12 to 22 carbon atoms, or short and contain from 1 to 3 carbon atoms.

When $R_{25}$ is a hydrocarbon-based group $R_{29}$, it preferably contains 1 to 3 carbon atoms.

Advantageously, $R_{24}$, $R_{26}$ and $R_{28}$, which may be identical or different, are chosen from linear or branched, saturated or unsaturated, $C_{11}$-$C_{21}$ hydrocarbon-based groups, and more particularly from linear or branched, saturated or unsaturated, $C_{11}$-$C_{21}$ alkyl and alkenyl groups.

Preferably, x and z, which may be identical or different, are 0 or 1.

Advantageously, y is equal to 1.

Preferably, r, s and t, which may be identical or different, are 2 or 3, and even more particularly are equal to 2.

The anion $X^-$ is preferably a halide, preferably chloride, bromide or iodide, a $(C_1$-$C_4)$alkyl sulphate, or a $(C_1$-$C_4)$alkyl- or $(C_1$-$C_4)$alkylarylsulphonate. However, it is possible to use methanesulphonate, phosphate, nitrate, tosylate, an anion derived from an organic acid, such as acetate or lactate, or any other anion that is compatible with the ammonium containing an ester function.

The anion $X^-$ is even more particularly chloride, methyl sulphate or ethyl sulphate.

Use is more particularly made, in the composition according to the invention, of the ammonium salts of formula (X) in which:
$R_{22}$ denotes a methyl or ethyl group,
x and y are equal to 1,
z is equal to 0 or 1,
r, s and t are equal to 2,
$R_{23}$ is chosen from the group $R_{26}$—C(O)—; methyl, ethyl or $C_{14}$-$C_{22}$ hydrocarbon-based groups, and a hydrogen atom,
$R_{25}$ is chosen from a hydrogen atom and the group $R_{28}$—C(O)—,
$R_{24}$, $R_{26}$ and $R_{28}$, which may be identical or different, are chosen from linear or branched, saturated or unsaturated, $C_{13}$-$C_{17}$ hydrocarbon-based groups and preferably from linear or branched, saturated or unsaturated, $C_{13}$-$C_{17}$ alkyl and alkenyl groups.

Advantageously, the hydrocarbon-based radicals are linear.

Among the compounds of formula (X), mention may, for example, be made of the salts, in particular the diacyloxyethyldimethylammonium, diacyloxyethyl-hydroxyethylmethylammonium, monoacyloxyethyldihydroxyethylmethylammonium or triacyloxyethylmethylammonium chloride or diacyloxyethyldimethylammonium, diacyloxyethylhydoxyethylmethylammonium, monoacyloxyethyldihydroxyethyl-methylammonium, triacyloxyethylmethylammonium or monoacyloxyethylhydroxyethyldimethylammonium methyl sulphate, and mixtures thereof. The acyl groups preferably have 14 to 18 carbon atoms and originate more particularly from a plant oil such as palm oil or sunflower oil. When the compound contains several acyl groups, these groups may be identical or different.

These products are obtained, for example, by direct esterification of triethanolamine, triisopropanolamine, an alkyldiethanolamine or an alkyldiisopropanolamine, which are optionally oxyalkylenated, with fatty acids or with fatty acid mixtures of plant or animal origin, or by transesterification of the methyl esters thereof. This esterification is followed by a quaternization by means of an alkylating agent such as an alkyl halide, preferably methyl or ethyl halide, a dialkyl sulphate, preferably dimethyl or diethyl sulphate, methyl methanesulphonate, methyl para-toluenesulphonate, glycol chlorohydrin or glycerol chlorohydrin.

Such compounds are, for example, sold under the names Dehyquart® by the company Henkel, Stepanquat® by the company Stepan, Noxamium® by the company Ceca or Rewoquat® WE 18 by the company Rewo-Witco.

The composition according to the invention may contain, for example, a mixture of quaternary ammonium salts of mono-, di- and triesters with a weight majority of diester salts.

Use may also be made of the ammonium salts containing at least one ester function that are described in patents U.S. Pat. Nos. 4,874,554 and 4,137,180.

Use may be made of behenoylhydroxypropyltrimethylammonium chloride sold by Kao under the name Quartam in BTC 131.

Preferably, the ammonium salts containing at least one ester function contain two ester functions.

Among the cationic surfactants that may be present in the composition according to the invention, it is more particularly preferred to choose the cetyltrimethylammonium, behenyltrimethylammonium and dipalmitoylethylhydroxy-ethylmethylammonium salts, and mixtures thereof, and more particularly behenyltrimethylammonium chloride, cetyltrimethylammonium chloride and dipalmitoylethylhydroxyethylammonium methosulphate, and mixtures thereof.

The cationic surfactant(s) that can be used according to the invention is (are) generally present in amounts preferably ranging from 0.01% to 20% by weight, in particular from 0.05% to 10% by weight, and even better still from 0.1% to 5% by weight, relative to the total weight of the composition.

The composition according to the invention may also comprise one or more non-silicone cationic polymers.

The cationic polymer(s) that can be used in accordance with the present invention can be chosen from any of those already known per se as improving the cosmetic properties of hair treated with detergent compositions, namely, in particular, those described in patent application EP-A-0 337 354 and in French patent applications FR-A-2 270 846, FR-A-2 383 660, FR-A-2 598 611, FR-A-2 470 596, FR-A-2 519 863 and FR-A-2 875 503.

The preferred cationic polymer(s) is (are) chosen from those which contain in their structure units comprising primary, secondary, tertiary and/or quaternary amine groups which can, for example, be either part of the main polymer chain, or be formed by a side substituent directly linked thereto.

Among the cationic polymers, mention may more particularly be made of polymers of the family of polyamines, polyamino amides and polyquarternary ammoniums.

Among these polymers, mention may be made of:

(1) Crosslinked or noncrosslinked homopolymers or copolymers derived from acrylic or methacrylic esters or amides and comprising at least one of the units of formula (XI), (XII), (XIII) or (XIV) below:

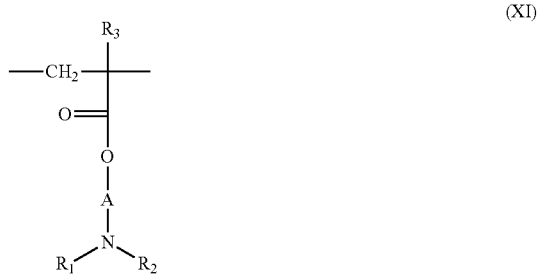

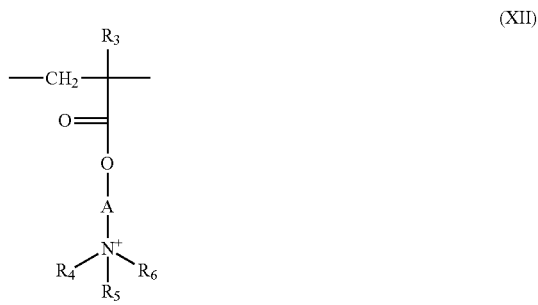

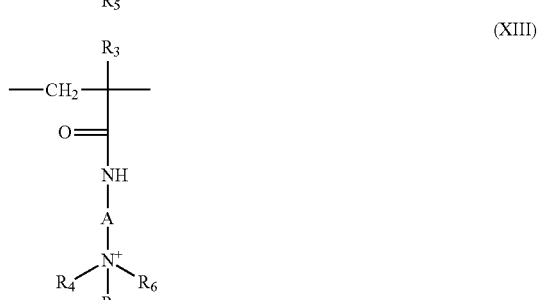

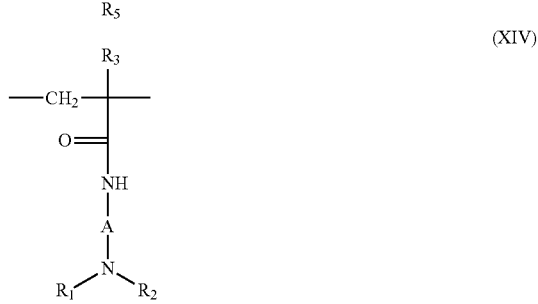

in which
$R_1$ and $R_2$, which may be identical or different, each represent a hydrogen atom or an alkyl group containing from 1 to 6 carbon atoms, and preferably methyl or ethyl;

$R_3$, which may be identical or different, each denote a hydrogen atom or a $CH_3$ group;

A, which may be identical or different, each represent a linear or branched alkyl group of 1 to 6 carbon atoms, preferably 2 or 3 carbon atoms, or a hydroxyalkyl group of 1 to 4 carbon atoms;

$R_4$, $R_5$, and $R_6$, which may be identical or different, each represent an alkyl group containing from 1 to 6 carbon atoms or a benzyl group, and preferably an alkyl group containing from 1 to 6 carbon atoms;

$X^-$ denotes an anion derived from an inorganic or organic acid, such as a methosulphate anion or a halide such as chloride or bromide.

The polymers of family (1) can also contain one or more unit(s) derived from comonomers which may be chosen from the family of acrylamides, methacrylamides, diacetone acrylamides, acrylamides and methacrylamides substituted on the nitrogen with lower ($C_1$-$C_4$) alkyls, acrylic or methacrylic acids or esters thereof, vinyllactams such as vinylpyrrolidone or vinylcaprolactam, and vinyl esters.

Thus, among these polymers of family (1), mention may be made of:

copolymers of acrylamide and of dimethylaminoethyl methacrylate quaternized with dimethyl sulphate or with a dimethyl halide, such as the product sold under the name Hercofloc by the company Hercules, copolymers of acrylamide and of methacryloyloxyethyltrimethylammonium chloride which are described, for example, in patent application EP-A-080976 and are sold under the name Bina Quat P 100 by the company Ciba Geigy, the copolymer of acrylamide and of methacryloyloxyethyltrimethylammonium methosulfate sold under the name Reten by the company Hercules, quaternized or non-quaternized vinylpyrrolidone/dialkylaminoalkyl acrylate or methacrylate copolymers, such as the products sold under the name Gafquat by the company ISP, for instance Gafquat 734 or Gafquat 755 (Polyquaternium-11) or alternatively the products known as Copolymer 845, 958 and 937. These polymers are described in detail in French patents 2 077 143 and 2 393 573. Polyquaternium-11 is preferably used, dimethylaminoethyl methacrylate/vinylcaprolactam/vinylpyrrolidone terpolymers, such as the product sold under the name Gaffix VC 713 by the company ISP, vinylpyrrolidone/methacrylamidopropyldimethylamine copolymers sold in particular under the name Styleze CC 10 by ISP, quaternized vinylpyrrolidone/dimethylaminopropylmethacrylamide copolymers such as the product sold under the name Gafquat HS 100 by the company ISP, and the crosslinked polymers of methacryloyloxy($C_1$-$C_4$)alkyltri($C_1$-$C_4$)alkyl-ammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with an olefinically unsaturated compound, more particularly methylenebisacrylamide. A crosslinked acrylamide/methacryloyloxyethyltrimethyl-ammonium chloride copolymer (20/80 by weight) in the form of a dispersion containing 50% by weight of the said copolymer in mineral oil can be used more particularly. This dispersion is sold under the name Salcare® SC 92 by the company Ciba. Use may also be made of a crosslinked homopolymer of methacryloyloxyethyltrimethylammonium chloride containing approximately 50% by weight of the homopolymer in mineral oil or in a liquid ester. These dispersions are sold under the names Salcare® SC 95 and Salcare® SC 96 by the company Ciba.

(2) Cationic polysaccharides in particular chosen from:

a) the cellulose ether derivatives comprising quaternary ammonium groups described in French patent 1 492 597, and in particular the polymers sold under the names JR (JR 400, JR 125, JR 30M) or LR (LR 400, LR 30M) by the company Union Carbide Corporation. These polymers are also defined in the CTFA dictionary as quaternary ammoniums of hydroxyethylcellulose having reacted with an epoxide substituted with a trimethylammonium group, b) cellulose copolymers or cellulose derivatives grafted with a water-soluble quaternary ammonium monomer, such as hydroxyalkylcelluloses, for instance hydroxymethyl-, hydroxyethyl- or hydroxypropylcelluloses grafted in particular with a methacryloylethyltrimethylammonium, methacrylamidopropyltrimethylammonium or dimethyldiallylammonium salt.

The products sold that correspond to this definition are more particularly the products corresponding to the INCI name Polyquaternium-4, under the name Celquat L 200 and Celquat H 100 by the company National Starch or Celquat LOR by the company Akzo Nobel, c) guar gums containing trialkylammonium cationic groups. Guar gums modified with a 2,3-epoxypropyltrimethylammonium salt (for example a chloride salt) are for example used.

Such products are sold in particular under the trade names Jaguar C13 S, Jaguar C 15, Jaguar C 17 or Jaguar C 162 by the company Meyhall.

(3) Polymers consisting of piperazinyl units and of divalent alkylene or hydroxyalkylene radicals containing straight or branched chains, optionally interrupted with oxygen, sulphur or nitrogen atoms or with aromatic or heterocyclic rings, and also the oxidation and/or quaternization products of these polymers. Such polymers are described, in particular, in French patents 2 162 025 and 2 280 361.

(4) Water-soluble cationic polyamino amides prepared in particular by polycondensation of an acid compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine or a bis-alkyl halide or alternatively with an oligomer resulting from the reaction of a difunctional compound which is reactive with respect to a bis-halohydrin, a bis-azetidinium, a bis-haloacyldiamine, a bis-alkyl halide, an epihalohydrin, a diepoxide or a bis-unsaturated derivative; these polyamino amides can be alkylated or, if they contain one or more tertiary amine functions, they can be quaternized. Such polymers are described, in particular, in French patents 2 252 840 and 2 368 508.

(5) Polyamino amide derivatives resulting from the condensation of polyalkylene polyamines with polycarboxylic acids followed by alkylation with difunctional agents. Mention may be made, for example, of adipic acid/dialkylaminohydroxy-alkyldialkylenetriamine polymers in which the alkyl group contains from 1 to 4 carbon atoms and preferably denotes methyl, ethyl or propyl. Such polymers are in particular described in French patent 1 583 363.

Among these derivatives, mention may be made more particularly of adipic acid/dimethylaminohydroxypropyl/diethylenetriamine polymers sold under the name Cartaretine F, F4 or F8 by the company Sandoz.

(6) Polymers obtained by reaction of a polyalkylene polyamine containing two primary amine groups and at least one secondary amine group with a dicarboxylic acid chosen from diglycolic acid and saturated aliphatic dicarboxylic acids having from 3 to 6 carbon atoms. The molar ratio between the polyalkylene polyamine and the dicarboxylic acid is between 0.8:1 and 1.4:1; the polyamino amide resulting therefrom is reacted with epichlorohydrin in a molar ratio of epichlorohydrin relative to the secondary amine group of the polyamino amide of between 0.5:1 and 1.8:1. Such polymers are described in particular in U.S. Pat. Nos. 3,227,615 and 2,961,347.

Polymers of this type are sold in particular under the name Hercosett 57 by the company Hercules Inc. or alternatively under the name PD 170 or Delsette 101 by the company Hercules in the case of the adipic acid/epoxypropyl/diethylene-triamine copolymer.

(7) Copolymers of alkyldiallylamine or of dialkyldiallylammonium, such as homopolymers or copolymers comprising, as main constituent of the chain, units corresponding to formula (XV) or (XVI):

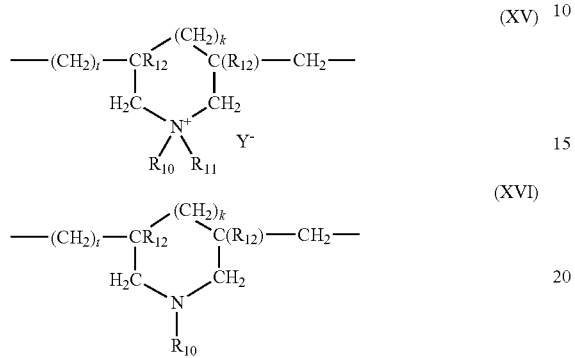

in which k and t are equal to 0 or 1, the sum k+t being equal to 1; $R_{12}$ denotes a hydrogen atom or a methyl group; $R_{10}$ and $R_{11}$ each denote, independently of one another, an alkyl group containing from 1 to 6 carbon atoms, a hydroxyalkyl group in which the alkyl group preferably contains from 1 to 5 carbon atoms, or a lower amidoalkyl group (i.e. the alkyl part of which is $C_1$-$C_4$), or else $R_{10}$ and $R_{11}$ can denote, together with the nitrogen atom to which they are attached, a heterocyclic group, such as piperidinyl or morpholinyl; $Y^-$ is an anion such as bromide, chloride, acetate, borate, citrate, tartrate, bisulphate, bisulphite, sulphate or phosphate. These polymers are in particular described in French patent 2 080 759 and in its certificate of addition 2 190 406.

Preferably, $R_{10}$ and $R_{11}$ each denote, independently of one another, an alkyl group containing from 1 to 4 carbon atoms.

Among the polymers defined above, mention may be made of dialkyldiallylammonium chloride homopolymers, more particularly the dimethyldiallylammonium chloride homopolymer (INCI name: Polyquaternium-6) sold under the name Merquat® 100 by the company Nalco (and its homologues of low weight-average molecular weights) and dialkyldiallylammonium chloride copolymers, more particularly the copolymer of dimethyldiallylammonium chloride and of acrylamide sold under the name Merquat® 550.

(8) The diquaternary ammonium polymers containing repeating units corresponding to formula (XVII):

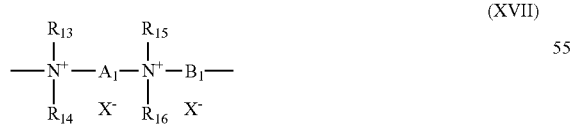

in which:

$R_{13}$, $R_{14}$, $R_{15}$ and $R_{16}$, which may be identical or different, represent aliphatic, alicyclic or arylaliphatic groups containing from 1 to 6 carbon atoms or lower hydroxyalkylaliphatic groups (i.e. the alkyl part of which is $C_1$-$C_4$) or alternatively $R_{13}$, $R_{14}$, $R_{15}$ and $R_{16}$, together or separately, constitute, with the nitrogen atoms to which they are attached, heterocycles optionally containing a second heteroatom other than nitrogen, or alternatively $R_{13}$, $R_{14}$, $R_{15}$ and $R_{16}$ each represent a linear or branched $C_1$-$C_6$ alkyl group substituted with a nitrile, ester, acyl, amide or —CO—O—$R_{17}$-E or —CO—NH—$R_{17}$-E group, where $R_{17}$ is an alkylene group and E is a quaternary ammonium group;

$A_1$ and $B_1$ represent polymethylene groups containing from 2 to 8 carbon atoms, which may be linear or branched, and saturated or unsaturated, and which may contain, linked to or inserted in the main chain, one or more aromatic rings, or one or more oxygen or sulphur atoms, or sulphoxide, sulphone, disulphide, amino, alkylamino, hydroxyl, quaternary ammonium, ureido, amide or ester groups, and $X^-$ denotes an anion derived from an inorganic or organic acid;

$A_1$, $R_{13}$ and $R_{15}$ can form, with the two nitrogen atoms to which they are attached, a piperazine ring; in addition, if $A_1$ denotes a linear or branched, saturated or unsaturated, alkylene or hydroxyalkylene group, $B_1$ can also denote a group:

—$(CH_2)_n$—CO-E'-OC—$(CH_2)_n$— in which n denotes an integer from 0 to 7 and E' denotes:
a) a glycol residue of formula —O—Z—O—, in which Z denotes a linear or branched hydrocarbon-based group, or a group corresponding to one of the following formulae:

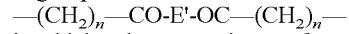

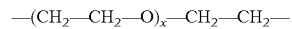

where x and y each denote an integer from 1 to 4, representing a defined and unique degree of polymerization or any number from 1 to 4 representing an average degree of polymerization;
b) a bis-secondary diamine residue such as a piperazine derivative;
c) a bis-primary diamine residue of formula —NH—Y—NH—, where Y denotes a linear or branched hydrocarbon-based group or alternatively the divalent group —$CH_2$—$CH_2$—S—S—$CH_2$—$CH_2$—;
d) a ureylene group of formula —NH—CO—NH—.

Preferably, $X^-$ is an anion such as chloride or bromide.

Polymers of this type are in particular described in French patents 2 320 330, 2 270 846, 2 316 271, 2 336 434 et 2 413 907 and patents U.S. Pat. Nos. 2,273,780, 2,375,853, 2,388, 614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

Use may more particularly be made of the polymers which consist of repeating units corresponding to formula (XVIII):

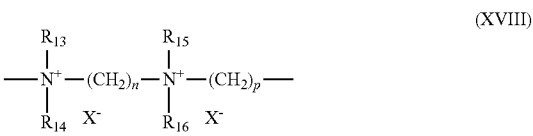

in which $R_{13}$, $R_{14}$, $R_{15}$ and $R_{16}$, which may be identical or different, each denote an alkyl or hydroxyalkyl group containing from 1 to 4 carbon atoms approximately, n and p are integers ranging from 2 to 8 approximately, and $X^-$ is an anion derived from an inorganic or organic acid. Preferably, $R_{13}$, $R_{14}$, $R_{15}$ and $R_{16}$ each denote a methyl group. By way of example of a polymer that can be used and that corresponds to formula (XVIII), mention may be made of the hexadimethrine chloride sold under the name Mexomere PO by the company Chimex.

(9) Polyquarternary ammonium polymers consisting of units of formula (XIX):

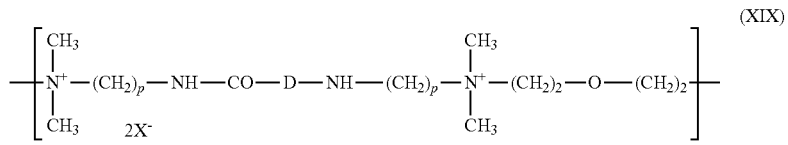

in which:
p denotes an integer ranging from 1 to 6 approximately,
D may be nothing or may represent a group —$(CH_2)_r$—CO—
  in which r denotes a number equal to 4 or to 7, and
$X^-$ is an anion derived from an inorganic or organic acid.

The cationic polymers comprising units of formula (XIII) are in particular described in patent application EP-A-122 324 and can be prepared according to the processes described in U.S. Pat. No. 4,157,388, 4,390,689, 4,702,906 and 4,719,282.

Among these polymers, preference is given to those having a molecular weight measured by carbon 13 NMR of less than 100 000, and in the formula of which: p is equal to 3, and
a) D represents a group —$(CH_2)_4$—CO—, X denotes a chlorine atom, the molecular weight measured by carbon 13 NMR ($^{13}$C NMR) being approximately 5600; a polymer of this type is sold by the company Miranol under the name Mirapol-AD1,
b) D represents a group —$(CH_2)_7$—CO—, X denotes a chlorine atom, the molecular weight measured by carbon 13 NMR ($^{13}$C NMR) being approximately 8100; a polymer of this type is sold by the company Miranol under the name Mirapol-AZ1,
c) D denotes the value zero, X denotes a chlorine atom, the molecular weight measured by carbon 13 NMR ($^{13}$C NMR) being approximately 25 500; a polymer of this type is sold by the company Miranol under the name Mirapol-A15,
d) A block copolymer made up of units corresponding to the polymers described in paragraphs a) and c), sold by the company Miranol under the names Mirapol-9, ($^{13}$C NMR molecular weight approximately 7800), Mirapol-175 ($^{13}$C NMR molecular weight approximately 8000), and Mirapol-95 ($^{13}$C NMR molecular weight approximately 12 500).

Even more particularly, the polymer comprising units of formula (XI) in which p is equal to 3, D denotes the value zero, and X denotes a chorine atom, the molecular weight measured by carbon 13 NMR ($^{13}$C NMR) being approximately 25 500, is preferred according to the invention.
(10) Quaternary polymers of vinylpyrrolidone and of vinylimidazole, such as, for example, the products sold under the names Luviquat FC 905, FC 550 and FC 370 by the company BASF.
(11) Cationic polyamines such as the Polyquart H sold by Henkel, referenced under the name Polyethylene Glycol (15) Tallow Polyamine in the CTFA dictionary.
(12) Vinylamide homopolymers or copolymers and in particular partially hydrolysed vinylamide homopolymers, such as poly(vinylamine/vinylamide). These polymers are made up of at least one vinylamide monomer corresponding to the following formula:

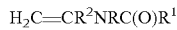

in which R, $R^1$ and $R^2$ are each chosen from a hydrogen atom, a $C_1$-$C_{20}$ alkyl group, an aryl group and an alkylaryl group of which the alkyl part contains from 1 to 20 carbon atoms.

In particular, said monomer may be chosen from N-vinylformamide, N-methyl-N-vinylacetamide and N-vinylacetamide. Preferably, the poly(vinylamine/N-vinyl-formamide) as sold under the name Catiofast VMP by the company BASF or under the name Lupamin 9030 by the company BASF is used.

These polymers can be formed, for example, by radical polymerization of a vinylamide monomer and then partial acid or basic hydrolysis of the amide functions to give quaternizable amine functions, as described in applications WO 2007/005577, U.S. Pat. Nos. 5,374,334, 6,426,383 and 6,894,110.
(13) Cationic polyurethanes.
(14) Other cationic polymers that can be used in the context of the invention are cationic proteins or cationic protein hydrolysates, polyalkyleneimines, in particular polyethyleneimines, polymers containing vinylpyridine or vinylpyridinium units, and chitin derivatives.

Among all the cationic polymers that can be used in the context of the present invention, the polymers of families (1), (2) and (7) and in particular copolymers of hydroxyethylcellulose and of diallyldimethylammonium chloride (polyquaternium-4) or of polyquaternium-11 are preferably used in the composition according to the invention.

In the event of cationic polymers being present, the composition according to the invention may comprise from 0.001% to 5% by weight, in particular from 0.01% to 2% by weight of cationic polymer(s), relative to the total weight of the composition.

The composition according to the invention may comprise one or more cosmetic additives commonly used in the art, such as, for example, antioxidants, organic ultraviolet-screening agents, inorganic ultraviolet-screening agents, thickeners, demulcents, antifoams, moisturizers, emollients, plasticizers, mineral fillers, clays, colloidal minerals, pearlescent agents, fragrances, peptizers, preservatives, fixing or nonfixing polymers other than the cationic polymers mentioned above, proteins, vitamins, antidandruff agents and mixtures of these compounds.

Those skilled in the art will take care to select the optional additives and the amounts thereof in such a way that they are not detrimental to the properties of the compositions of the present invention.

When they are present, these additives can individually represent an amount ranging from 0.001% to 90% by weight, preferably from 0.001% to 50%, better still from 0.001% to 20% by weight, relative to the total weight of the composition according to the invention.

The composition according to the invention generally comprises water or a mixture of water and of one or more organic solvents.

By way of organic solvent, mention may be made of lower ($C_1$-$C_4$) alcohols such as ethanol, isopropanol, tert-butanol or n-butanol; polyols such as propylene glycol and glycerol; polyol ethers; $C_5$-$C_{10}$ alkanes; $C_3$-$C_4$ ketones, such as acetone; $C_1$-$C_4$ alkyl acetates, such as methyl acetate, ethyl acetate and butyl acetate; dimethoxyethane, diethoxyethane; and mixtures thereof.

When the composition according to the invention comprises one or more organic solvents, they may be present in a proportion of from 0.1 to 30% by weight, preferably from 0.1 to 10% by weight, of the total weight of the composition.

The pH of the composition according to the invention, if said composition is aqueous, generally ranges from 1.5 to 11, and preferably from 2 to 6.5. It may be adjusted to the desired value by means of one or more acidifying or basifying agent(s) usually used in the dyeing of keratin fibres, or alternatively using one or more standard buffer system(s).

Among the acidifying agents, examples that may be mentioned include inorganic or organic acids, for instance hydrochloric acid, orthophosphoric acid, sulphuric acid and sulphonic acids, and carboxylic acids, for instance acetic acid, tartaric acid, citric acid and lactic acid.

Among the basifying agents, mention may be made, by way of example, of aqueous ammonia, alkali metal carbonates, alkanolamines such as mono-, di- and triethanolamines and also derivatives thereof, sodium hydroxide, potassium hydroxide and the compounds of formula (XX) below:

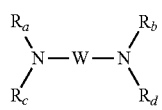

(XX)

in which:

W is a propylene residue optionally substituted with a hydroxyl group or a $C_1$-$C_4$ alkyl radical;

$R_a$, $R_b$, $R_c$ and $R_d$, which may be identical or different, represent a hydrogen atom or a $C_1$-$C_4$ alkyl or $C_1$-$C_4$ hydroxyalkyl group.

The composition according to the invention may be in any of the galenical forms normally used for topical application. In particular, the composition according to the invention may be a lotion, a gel, a spray, a mousse or a cream.

The composition according to the invention may be a shampoo, a conditioner, a hair shaping product, a dyeing product, a bleaching product or a permanent-waving product.

Preferably, the composition according to the invention is a conditioner.

Another subject of the invention is a cosmetic treatment process which comprises the application to keratin fibres, preferably human keratin fibres such as the hair, and the scalp, of a composition according to the invention as described above, with or without, and preferably without, subsequent rinsing of said keratin fibres.

The composition according to the invention that is applied can be massaged onto the hair in order to accelerate penetration thereof, by hand or using any other suitable means, such as a brush or a comb.

The examples which follow are intended to illustrate the invention without, however, being limiting in nature.

The amounts are indicated therein as percent by weight of active material (A.M.) relative to the total weight of each composition.

EXAMPLE 1

Rinse-out Conditioner

| | |
|---|---|
| Hydroxyethylcellulose (Natrosol 250 HHR - Aqualon) | 1 |
| Amodimethicone as a nonionic emulsion containing 15% AM (Wacker Belsil ADM LOG 1 - Wacker) | 0.45 g AM |
| Zinc gluconate (Givobio G Zn - SEPPIC) | 6.5 |
| pH 5-5.5 | |
| Demineralized water | qs100 g |

EXAMPLE 2

Rinse-out Conditioner

| | |
|---|---|
| Hydroxyethylcellulose (Natrosol 250 HHR - Aqualon) | 1 |
| Amodimethicone as a cationic emulsion containing 35% AM (Dow Corning 939 Emulsion - Dow Corning) | 0.88 g AM |
| Zinc chloride (zinc chloride - Honeywell) | 6.5 |
| pH 5-5.5 | |
| Demineralized water | qs100 g |

EXAMPLE 3

Rinse-out Conditioner

| | % AM |
|---|---|
| Cetyl alcohol (Lanette 16 sold by the company Cognis) | 3.7 |
| Myristyl/cetyl/stearyl myristate/palmitate/stearate mixture (Crodamol MS-PA - Croda) | 0.8 |
| Myristyl alcohol (Lanette 14 sold by the company Cognis) | 0.4 |
| Hydroxyethylcellulose (Natrosol 250 HHR sold by the company Aqualon) | 1 |
| Cetyltrimethylammonium chloride (Arquad 16-25 LO sold by the company Akzo Nobel) | 0.63 |
| Behenyltrimethylammonium chloride (Genamin KDMP sold by the company Clariant) | 0.48 |
| Cetearyl alcohol (70%)/dipalmitoylethylhydroxyethylammonium methosulphate (30%) mixture (Dehyquart F30 sold by the company Cognis) | 1 |
| Amodimethicone as a nonionic emulsion containing 15% AM (Wacker Belsil ADM LOG 1 sold by the company Wacker) | 0.56 |
| Zinc gluconate | 5 |
| Preserving agents | 0.33 |
| Fragrance | 0.4 |
| Citric acid qs | pH 3.5 |
| Demineralized water | qs 100 g |

EXAMPLE 4

Rinse-out Conditioner

| | % AM |
|---|---|
| Cetyl alcohol (Lanette 16 sold by the company Cognis) | 3.7 |
| Myristyl/cetyl/stearyl myristate/palmitate/stearate mixture (Crodamol MS-PA - Croda) | 0.8 |

-continued

| | % AM |
|---|---|
| Myristyl alcohol (Lanette 14 sold by the company Cognis) | 0.4 |
| Hydroxyethylcellulose (Natrosol 250 HHR sold by the company Aqualon) | 1 |
| Cetyltrimethylammonium chloride (Arquad 16-25 LO sold by the company Akzo Nobel) | 0.75 |
| Amodimethicone (Wacker Belsil ADM LOG 1 sold by the company Wacker) | 0.56 |
| Zinc sulphate (zinc sulphate sold by the company Merck) | 4 |
| Preserving agents | 0.33 |
| Fragrance | 0.4 |
| Citric acid qs | pH 3.5 |
| Demineralized water | qs 100 g |

EXAMPLE 5

Rinse-out Conditioner

| | |
|---|---|
| Cetyl alcohol (Lanette 16 sold by the company Cognis) | 7 |
| Cetyl/stearyl ester (Crodamol MS-PA sold by the company Croda) | 1.5 |
| Behenyltrimethylammonium chloride (Genamin KDMP sold by the company Clariant) | 5 |
| Amodimethicone (Dow Corning DC2-8299 Cationic Emulsion) | 1.71 |
| Zinc gluconate (Givobio G Zn from SEPPIC | 6.5 |
| Preserving agents | 0.3 |
| Fragrance | 0.4 |
| Citric acid qs | pH 3.5 |
| Demineralized water | qs 100 g |

EXAMPLE 6

Rinse-out Conditioner

| | |
|---|---|
| Cetyl alcohol (Lanette 16 sold by the company Cognis) | 2.5 |
| Cetyl/stearyl ester (Crodamol MS-PA sold by the company Croda) | 0.5 |
| Behenyltrimethylammonium chloride (Genamin KDMP sold by the company Clariant) | 1.2 |
| Amodimethicone (Dow Corning DC939 Cationic Emulsion) | 1.4 |
| Zinc chloride | 4 |
| Citric acid qs | pH 3.5 |
| Demineralized water | qsp 100% |

EXAMPLE 7

Leave-in Conditioner

| | % AM |
|---|---|
| Polyquaternium-4 (Celquat LOR sold by the company Akzo Nobel) | 0.13 |
| Polyquaternium-11 (Gafquat 755 sold by the company ISP) | 0.03 |
| Amodimethicone (Dow Corning 939 emulsion sold by the company Dow Corning) | 0.12 |
| Oleylhydroxyethyldimethylammonium chloride (Chimexane CL sold by the company Chimex) | 0.03 |
| Phenoxyethanol (Sepicide LD sold by the company SEPPIC) | 0.7 |
| Caprylyl glycol (Dermosoft Octiol sold by the company Dr Straetmans) | 0.1 |

-continued

| | % AM |
|---|---|
| Fragrance | 0.2 |
| PEG-40 hydrogenated castor oil (Emulgin HRE 40 sold by the company Cognis) | 0.6 |
| Zinc gluconate (Givobio G Zn sold by the company SEPPIC) | 0.5 |
| Lactic acid (Purac HS 90 sold by the company Purac) | qs pH 3.5 |
| Demineralized water | qs 100 g |

The formulae of the 7 examples are stable over time and, when these formulae are applied to wet hair, the dried hair has a smooth feel, is easy to disentangle and has been given mass.

A composition according to the invention (composition 3) was compared with a comparative composition (composition 3B) not comprising zinc salt. When applied to wet hair, composition 3 provides easy disentangling, greater sheen and more body on dry hair than composition 3B.

The invention claimed is:
1. A cosmetic composition comprising:
   at least one non-nitrogenous zinc salt chosen from organic salts, and
   at least one amino silicone,
   wherein the weight ratio of the amount of the at least one amino silicone to the amount of zinc element ranges from about 0.01 to about 5.
2. The composition according to claim 1, wherein the at least one non-nitrogenous zinc salt is chosen from inorganic salts.
3. The composition according to claim 1, wherein the at least one non-nitrogenous zinc salt is chosen from at least one of zinc lactate, zinc gluconate, zinc phenolsulphonate, zinc citrate, zinc salicylate and its derivatives corresponding to the formula:

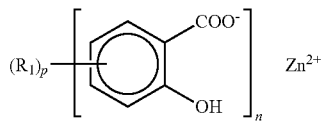

wherein:
   n is 2, p is chosen from 0, 1, 2 and 3; and
   $R_1$ is chosen from linear and branched $C_1$-$C_{18}$ alkyl groups; linear and branched $C_1$-$C_{18}$ hydroxyalkyl groups; halogen atoms, $C_2$-$C_{18}$ acyl groups; $COR_2$; $OCOR_2$; and $CONHR_2$ groups,
   wherein $R_2$ is chosen from hydrogen atoms and linear and branched $C_1$-$C_{18}$ alkyl groups.
4. The composition according to claim 1, wherein the at least one non-nitrogenous zinc salt is chosen from zinc lactate and zinc gluconate.
5. The composition according to claim 1, wherein the at least one non-nitrogenous zinc salt is zinc gluconate.
6. The composition according to claim 1, wherein the concentration of the at least one non-nitrogenous zinc salt ranges from about 0.1 to about 10% by weight, relative to the total weight of the composition.
7. The composition according to claim 6, wherein the concentration of the at least one non-nitrogenous zinc salt ranges from about 0.5 to about 6.5% by weight, relative to the total weight of the composition.
8. The composition according to claim 1, wherein the concentration of the zinc element is less than about 2% by weight, relative to the total weight of the composition.

9. The composition according to claim 8, wherein the concentration of the zinc element ranges from about 0.1% to about 1% by weight, relative to the total weight of the composition.

10. The composition according to claim 1, wherein the weight ratio of the at least one amino silicone to the zinc element ranges from about 0.1 to about 3.

11. The composition according to claim 1, wherein the at least one amino silicone is chosen from:
(a) compounds of formula (I):

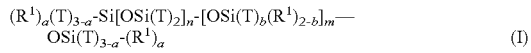

(I)

wherein,
T is independently chosen from hydrogen atoms, phenyl radicals, hydroxyl radicals, $C_1$-$C_8$ alkyl radicals, and $C_1$-$C_8$ alkoxy radicals,
a is independently chosen from the number 0 and integer ranging from 1 to 3,
b is independently chosen from 0 and 1,
m and n are numbers such that the sum (n+m) ranges from 1 to 2000, wherein n is a number ranging from 0 to 1999, and m is a number ranging from 1 to 2000;
$R^1$ is independently chosen from monovalent radicals of formula —$C_qH_{2q}L$, wherein q is independently chosen from numbers ranging from 2 to 8 and L is an optionally quaternized amino group chosen from the groups:
—$N(R^2)$—$CH_2$—$CH_2$—$N(R^2)_2$;
—$N(R^2)_2$; —$N^+(R^2)_3Q^-$;
—$N^+(R^2)(H)_2Q^-$;
—$N^+(R^2)_2HQ^-$; and
—$N(R^2)$—$CH_2$—$CH_2$—$N^+(R^2)(H)_2Q^-$,
wherein $R^2$ is independently chosen from hydrogen atoms, phenyl radicals, benzyl radicals, and saturated monovalent hydrocarbon-based radicals, and $Q^-$ is a halide ion;
(b) compounds of formula (IV) below:

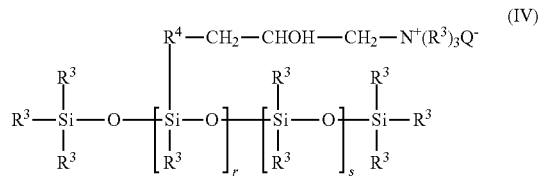

(IV)

wherein,
$R^3$ is independently chosen from $C_1$-$C_{18}$ monovalent hydrocarbon-based radicals;
$R^4$ is chosen from divalent hydrocarbon-based radicals;
$Q^-$ is a halide ion;
r is a mean statistical value ranging from about 2 to about 20; and
s is a mean statistical value ranging from about 20 to about 200;
c) quaternary ammonium silicones of formula (V):

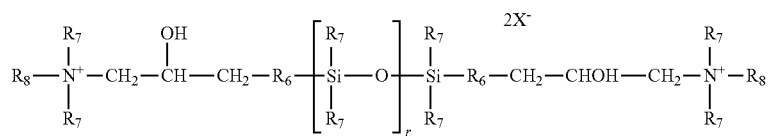

(V)

wherein:
$R_7$ is independently chosen from monovalent hydrocarbon-based radicals comprising from 1 to 18 carbon atoms;
$R_6$ is independently chosen from divalent hydrocarbon-based radicals;
$R_8$ is independently chosen from hydrogen atoms, monovalent hydrocarbon-based radicals comprising from 1 to 18 carbon atoms and radicals —$R_6$—NH-$COR_7$;
$X^-$ is chosen from anions and organic acid salts; and
r is a mean statistical value ranging from about 2 to about 200; and
d) amino silicones of formula (VI):

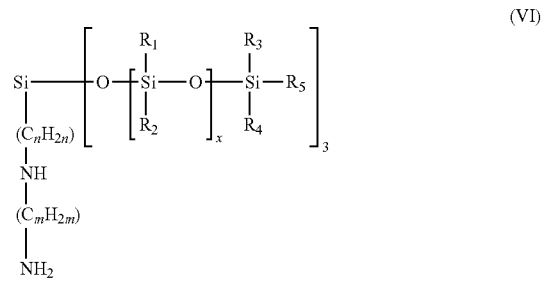

(VI)

wherein:
$R_1$, $R_2$, $R_3$ and $R_4$ are independently chosen from $C_1$-$C_4$ alkyl radicals and phenyl groups,
$R_5$ is chosen from $C_1$-$C_4$ alkyl radicals and hydroxyl groups,
n is an integer ranging from 1 to 5,
m is an integer ranging from 1 to 5, and
x is selected such that the amine number ranges from about 0.01 to about 1 meq/g.

12. The composition according to claim 1, wherein the concentration of the at least one amino silicone ranges from about 0.01 to about 10% by weight, relative to the total weight of the composition.

13. The composition according to claim 1, wherein the concentration of the at least one amino silicone ranges from about 0.1 to about 3% by weight, relative to the total weight of the composition.

14. The composition according to claim 1, further comprising at least one additional compound chosen from fatty alcohols, cationic polymers, and cationic surfactants.

15. The composition according to claim 1, wherein the composition is in the form of a leave-in care product.

16. A cosmetic treatment process for keratin fibers comprising
applying to the keratin fibers and scalp a composition comprising at least one non-nitrogenous zinc salt chosen from organic slats, and at least one amino silicone, wherein the weight ratio of the amount of the at least one amino silicone to the amount of zinc element ranges from about 0.01 to about 5; and optionally rinsing the composition.

17. A method of conditioning keratin fibers and protecting the artificial color of keratin fibers against fading, comprising applying to the keratin fibers a composition comprising at least one non-nitrogenous zinc salt chosen from organic salts, and at least one amino silicone, wherein the weight ratio of the at least one amino silicone to zinc element ranges from about 0.01 to about 5.

* * * * *